(12) United States Patent
Mohan et al.

(10) Patent No.: US 8,647,350 B2
(45) Date of Patent: Feb. 11, 2014

(54) DELIVERY DEVICE AND METHOD FOR COMPLIANT TISSUE FASTENERS

(75) Inventors: Ashik A. Mohan, Petaluma, CA (US); William K. Wheeler, Alamo, CA (US)

(73) Assignee: Raptor Ridge, LLC, Alamo, CA (US)

( * ) Notice: Subject to any disclaimer, the term of this patent is extended or adjusted under 35 U.S.C. 154(b) by 420 days.

(21) Appl. No.: 12/849,534

(22) Filed: Aug. 3, 2010

(65) Prior Publication Data

US 2011/0190809 A1     Aug. 4, 2011

Related U.S. Application Data

(60) Provisional application No. 61/233,011, filed on Aug. 11, 2009.

(51) Int. Cl.
*A61B 17/00* (2006.01)
(52) U.S. Cl.
USPC .......................................... 606/139; 606/205
(58) Field of Classification Search
USPC ............. 606/139–144, 205; 227/175.1–182.1
See application file for complete search history.

(56) References Cited

U.S. PATENT DOCUMENTS

| | | |
|---|---|---|
| 1,756,670 A | 4/1930 | Treat |
| 2,659,371 A | 11/1953 | Schnee |
| 3,361,133 A | 1/1968 | Kimberley et al. |
| 3,525,340 A | 8/1970 | Gilbert et al. |
| 3,746,002 A | 7/1973 | Haller |
| 3,993,076 A | 11/1976 | Fogarty |
| 4,016,883 A | 4/1977 | Wright, Jr. |
| 4,060,089 A | 11/1977 | Noiles |
| 4,241,861 A | 12/1980 | Fleischer |
| 4,257,419 A | 3/1981 | Goltner et al. |
| 4,271,828 A | 6/1981 | Angelchik |
| 4,390,019 A | 6/1983 | LeVeen et al. |
| 4,402,445 A | 9/1983 | Green |
| 4,489,725 A | 12/1984 | Casey et al. |
| 4,506,671 A | 3/1985 | Green |
| 4,548,201 A | 10/1985 | Yoon |
| 4,754,758 A | 7/1988 | Li |
| 4,805,617 A | 2/1989 | Bedi et al. |

(Continued)

FOREIGN PATENT DOCUMENTS

| | | |
|---|---|---|
| EP | 0 138 687 A1 | 4/1985 |
| FR | 2598905 A1 | 11/1987 |

(Continued)

OTHER PUBLICATIONS

Salzberg et al., "Surgical left atrial appendage occlusion: evaluation of a novel device with magnetic resonance imaging," Eur J Cardiothorac Surg 2008;34:766-770. Retrieved from the Internet: < http://ejcts.ctsnetjournals.org/cgi/reprint/34/4/766>.

(Continued)

*Primary Examiner* — Katherine Dowe

(57) ABSTRACT

Devices, systems, and methods for closing the base of a left atrial appendage or other tissue structure comprise a device applicator having jaws, a shaft, and a handle. First and second triggers on a handle are configured to close the jaws and a closure device in a step-wise manner where tissue penetrating fasteners within the closure device are engaged by studs on the jaws, where the studs must be released prior to the opening of the jaws.

19 Claims, 11 Drawing Sheets

(56) References Cited

U.S. PATENT DOCUMENTS

| | | | |
|---|---|---|---|
| 4,822,348 A | 4/1989 | Casey |
| 4,924,864 A | 5/1990 | Danzig |
| 4,988,355 A | 1/1991 | LeVeen et al. |
| 5,002,552 A | 3/1991 | Casey |
| 5,156,614 A | 10/1992 | Green et al. |
| 5,171,253 A | 12/1992 | Klieman |
| 5,193,554 A | 3/1993 | McQuilkin |
| 5,246,456 A | 9/1993 | Wilkinson |
| 5,257,999 A | 11/1993 | Slanetz, Jr. |
| 5,282,812 A | 2/1994 | Suarez, Jr. |
| 5,306,234 A | 4/1994 | Johnson |
| 5,336,232 A | 8/1994 | Green et al. |
| 5,358,506 A | 10/1994 | Green et al. |
| 5,358,510 A | 10/1994 | Luscombe et al. |
| 5,413,268 A | 5/1995 | Green et al. |
| 5,425,705 A | 6/1995 | Evard et al. |
| 5,441,507 A | 8/1995 | Wilk |
| 5,485,947 A | 1/1996 | Olson et al. |
| 5,507,797 A | 4/1996 | Suzuki et al. |
| 5,549,621 A | 8/1996 | Bessler et al. |
| 5,554,169 A | 9/1996 | Green et al. |
| 5,575,802 A | 11/1996 | McQuilkin et al. |
| 5,605,272 A | 2/1997 | Witt et al. |
| 5,620,452 A | 4/1997 | Yoon |
| 5,624,453 A | 4/1997 | Ahmed |
| 5,749,893 A | 5/1998 | Vidal et al. |
| 5,843,101 A | 12/1998 | Fry |
| 5,846,255 A | 12/1998 | Casey |
| 5,865,791 A | 2/1999 | Whayne et al. |
| 5,964,774 A | 10/1999 | McKean et al. |
| 6,051,003 A | 4/2000 | Chu et al. |
| 6,238,414 B1 | 5/2001 | Griffiths |
| 6,273,897 B1 | 8/2001 | Dalessandro et al. |
| 6,325,810 B1 | 12/2001 | Hamilton et al. |
| 6,338,710 B1 | 1/2002 | Takahashi et al. |
| 6,406,485 B1 | 6/2002 | Hossain et al. |
| 6,436,108 B1 | 8/2002 | Mears |
| 6,488,689 B1 | 12/2002 | Kaplan et al. |
| 6,579,304 B1 | 6/2003 | Hart et al. |
| 6,582,451 B1 | 6/2003 | Marucci et al. |
| 6,629,988 B2 | 10/2003 | Weadock |
| 6,663,653 B2 | 12/2003 | Akerfeldt |
| 6,692,507 B2 | 2/2004 | Pugsley et al. |
| 6,699,258 B1 | 3/2004 | Sadler et al. |
| 6,702,826 B2 | 3/2004 | Liddicoat et al. |
| 6,746,461 B2 | 6/2004 | Fry |
| 6,790,172 B2 | 9/2004 | Alferness et al. |
| 6,817,972 B2 | 11/2004 | Snow |
| 6,893,391 B2 | 5/2005 | Taylor |
| 6,974,462 B2 | 12/2005 | Sater |
| 7,077,856 B2 | 7/2006 | Whitman |
| 7,220,272 B2 | 5/2007 | Weadock |
| 7,422,783 B2 | 9/2008 | Tremblay et al. |
| 7,473,261 B2 | 1/2009 | Rennich |
| 7,569,064 B1 | 8/2009 | Hausen et al. |
| 7,645,285 B2 | 1/2010 | Cosgrove et al. |
| 7,658,312 B2 | 2/2010 | Vidal et al. |
| 7,686,759 B2 | 3/2010 | Sater |
| 7,794,475 B2 | 9/2010 | Hess et al. |
| 7,931,578 B2 | 4/2011 | Whayne et al. |
| 7,951,069 B2 | 5/2011 | Bertolero |
| 7,992,757 B2 | 8/2011 | Wheeler et al. |
| 2003/0125729 A1 | 7/2003 | Hooven et al. |
| 2004/0030335 A1 | 2/2004 | Zenati et al. |
| 2004/0073241 A1 | 4/2004 | Barry et al. |
| 2005/0125010 A1* | 6/2005 | Smith et al. ............ 606/142 |
| 2005/0149068 A1 | 7/2005 | Williams et al. |
| 2005/0149069 A1 | 7/2005 | Bertolero et al. |
| 2005/0149988 A1 | 7/2005 | Grannan |
| 2005/0149989 A1 | 7/2005 | Lupoi et al. |
| 2005/0154404 A1 | 7/2005 | Liddicoat et al. |
| 2005/0177182 A1 | 8/2005 | van Der Burg et al. |
| 2006/0004388 A1 | 1/2006 | Whayne et al. |
| 2006/0020162 A1 | 1/2006 | Whayne et al. |
| 2006/0100649 A1 | 5/2006 | Hart |
| 2007/0005108 A1 | 1/2007 | Simhon et al. |
| 2007/0060951 A1 | 3/2007 | Shannon |
| 2007/0149988 A1 | 6/2007 | Michler et al. |
| 2007/0149989 A1 | 6/2007 | Santilli et al. |
| 2007/0260278 A1* | 11/2007 | Wheeler et al. ............ 606/220 |
| 2008/0033457 A1 | 2/2008 | Francischelli et al. |
| 2008/0039879 A1 | 2/2008 | Chin et al. |
| 2008/0125795 A1 | 5/2008 | Kaplan et al. |
| 2008/0132891 A1 | 6/2008 | Nobis et al. |
| 2008/0208324 A1 | 8/2008 | Glithero et al. |
| 2008/0287989 A1 | 11/2008 | Weisel et al. |
| 2009/0012545 A1 | 1/2009 | Williamson, IV et al. |
| 2009/0171380 A1 | 7/2009 | Whiting |
| 2009/0187198 A1 | 7/2009 | Weitzner et al. |
| 2009/0209986 A1 | 8/2009 | Stewart et al. |
| 2010/0082047 A1 | 4/2010 | Cosgrove et al. |
| 2010/0115739 A1 | 5/2010 | Mathur |
| 2010/0179570 A1 | 7/2010 | Privitera et al. |
| 2010/0204716 A1 | 8/2010 | Stewart et al. |
| 2011/0009853 A1 | 1/2011 | Bertolero et al. |
| 2011/0230903 A1 | 9/2011 | Bertolero |
| 2011/0270303 A1 | 11/2011 | Wheeler et al. |
| 2012/0035631 A1 | 2/2012 | Hughett, Sr. et al. |
| 2012/0059400 A1 | 3/2012 | Williamson, IV et al. |
| 2012/0158022 A1 | 6/2012 | Kaplan et al. |

FOREIGN PATENT DOCUMENTS

| | | |
|---|---|---|
| GB | 1530282 A | 10/1978 |
| GB | 2177748 A | 1/1987 |
| GB | 2190297 A | 11/1987 |
| GB | 2226958 A | 7/1990 |

OTHER PUBLICATIONS

International Search Report and Written Opinion of PCT Patent Application No. PCT/US2010/045216, mailed Oct. 12, 2010, 8 pages total.
Amendment dated Jul. 22, 2011 for U.S. Appl. No. 13/117,863.
International search report and written opinion dated Sep. 17, 2008 for PCT/US2007/068147.
Office action dated Feb. 24, 2012 for U.S. Appl. No. 13/180,373.
Office action dated Dec. 7, 2010 for U.S. Appl. No. 11/744,135.
Response to final office action dated Aug. 1, 2012 for U.S. Appl. No. 11/155,305.
Response to office action dated Apr. 28, 2009 for U.S. Appl. No. 11/155,305.
Revised Brief on Appeal dated Sep. 7, 2010 for U.S. Appl. No. 11/003,696.

* cited by examiner

DELIVERY DEVICE AND METHOD FOR COMPLIANT TISSUE FASTENERS

CROSS-REFERENCES TO RELATED APPLICATIONS

This application claims the benefit of U.S. Provisional Application No. 61/233,011, filed on Aug. 11, 2009, the full disclosure of which is incorporated herein by reference.

The present application is related to but does not claim priority from U.S. application Ser. No. 11/744,135, the full disclosure of which is incorporated herein by reference.

BACKGROUND OF THE INVENTION

1. Field of the Invention

The present invention relates generally to medical devices, systems, and methods. More particularly, the present invention relates to tools, systems, and methods for delivering compliant fasteners and compression structures for tissue approximation, for example to isolate left atrial appendages and other tissue structures near their bases.

Atrial fibrillation is a relatively common condition characterized by a very rapid heart beat of the left and right atrium. While atrial fibrillation is not normally fatal itself, it has been associated with an increased risk of stroke. It is believed that the rapid heart beat causes blood to pool in the left atrial appendage which causes emboli that are released into the left atrium from where they can enter the cerebral vasculature, thus causing a stroke. In addition to stroke, the emboli can enter coronary circulation, potentially causing myocardial infarction, or can enter peripheral circulation, potentially causing peripheral vascular disease.

The risk of stroke in patients suffering from atrial fibrillation can be reduced in a variety of ways. For example, blood thinning drugs can be used to reduce the risk of clot formation. The use of blood thinners, however, is contraindicated in patients at risk of bleeding disorders.

More aggressive treatment protocols have been proposed which involve closing the left atrial appendage. Closure and excision may be performed in open surgical procedures, typically requiring the patient to be placed on by-pass and the chest to be opened through the sternum. Alternatively, thoracoscopic and other less invasive procedures have been proposed. U.S. Pat. No. 5,306,234 teaches the performance of beating heart procedures using otherwise conventional surgical techniques. The use of conventional techniques through small chest penetrations while the heart is beating can be difficult to perform. U.S. Pat. No. 5,865,791 describes an intravascular approach where tools are introduced through the vasculature and passed into the left atrium. The tools are used to ablate or fuse the left atrial appendage from the inside using energy, adhesives, or the like. The '791 patent also describes a thoracoscopic procedure where a tether is placed over the neck of the atrial appendage and tied off to achieve isolation. The '791 patent still further suggests other closure elements including sutures, staples, shape-memory wires, biocompatible adhesives, and the like. U.S. Pat. No. 6,488,689 describes a transpericardial procedure where the distal tip of the left atrial appendage is grasped and pulled backwardly through a capture loop which encircles the base of the left atrial appendage.

Of particular interest to the present invention, a compliant closure structure for the sealing of the left atrial appendage is described in co-pending, commonly owned U.S. Patent Publication 2007/0260278 (application Ser. No. 11/744,135), the full disclosure of which has been previously incorporated herein by reference. The compliant structure described in the '135 publication comprises an elastomeric body having a pair of opposed legs which may be arranged in an oval or a U-shaped configuration to define an opening therebetween. By placing the opening between the legs over the left atrial appendage and aligning it with the base of the appendage, the structure may be closed to provide the desired sealing. To hold the structure closed, a number of discrete, axially spaced-apart tissue penetrating fasteners are arranged along the lengths of each of the legs. By compressing the legs together to press-fit the fasteners, the compliant structure may be closed to provide a compliant seal which effectively isolates the left atrial appendage.

U.S. Patent Publication 2007/0260278 describes a particular delivery tool for the compliant closure structure. The delivery tool includes jaws which can be inserted into the legs of the closure structure and actuated to close the jaws in the legs over the left atrial appendage. The jaws further include comb studs which engage and press fit the fasteners in order to hold the compliant structure in its closed, sealing configuration. The studs are intended to be retracted to allow the delivery tool to be removed.

Although functional, the delivery tool of the '135 publication has certain shortcomings. For example, the actuation of the jaws and retraction of the comb studs can be performed out of order, increasing the risk that the delivery of the compliant structure will fail. Moreover, positioning and orientation of the delivery tool can be difficult, particularly when the tool is introduced through an intercostal penetration to access the left atrium. Additionally, the jaws in the device of the '278 publication are attached in the axial plane of the device shaft. Such a straight line of attachment can make it more difficult to align the jaws with the base of the appendage and across the os of the atrium leading into the appendage. If the closure device is not aligned across the base to completely close the os, gaps or openings (referred to as "cul-de-sacs") can remain at the site of closure, increasing the risk of thrombus formation in the atrium. The importance of forming a complete seal of the os which is free from such cul-de-sacs is discussed in Salzberg et al. (2008) Eur. J. Cardiothoracic Surg. 34:766-770.

For these reasons, it would be desirable to provide improved delivery tools for use with the tissue closure devices described in U.S. Patent Publication 2007/0260278. It would be further desirable if the delivery tools and methods of their use were compatible with the delivery of other tissue closure devices and for procedures in addition to closure of the left atrial appendage. At least some of these objectives will be met by the inventions described hereinbelow.

2. Description of the Background Art

Less invasive and other procedures for closing the left atrial appendage are described in U.S. Pat. Nos. 6,488,689; 5,865,791; and 5,306,234; and Published Application Nos. 2005/0154404 and 2004/0030335. Other tissue ligation tools and related devices and techniques are described in U.S. Pat. Nos. 6,790,172; 6,436,108; 6,325,810; 6,273,897; 6,051,003; 5,964,774; 5,624,453; 5,507,797; and 4,257,419. See also U.S. Patent Publication 2007/0260278 described above.

BRIEF SUMMARY OF THE INVENTION

The present invention provides a closure device applicator for use with a closure device including a compression body having two legs with opposed tissue-engaging surfaces and a plurality of tissue-penetrating fasteners deployable between said surfaces. Such compression bodies are described in co-pending, commonly-owned application U.S. Patent Publication 2007/0260278, the full disclosure of which has been previously incorporated herein by reference. The applicators of the present invention, however, would also find use with other closure devices having similar structures.

The closure device applicator of the present invention comprises a shaft, a handle attached to a proximal end of the shaft, and a pair of jaws pivotally attached to a distal end of the shaft. Each jaw has a plurality of retractable studs, where the jaws are adapted to removably engage and hold the legs of the tissue closure device with the studs engaging the individual fasteners in the closure device. The handle includes a first trigger and a second trigger. A linkage assembly, typically forming a shaft, joins the handle to the jaws, where the first trigger and the second trigger are retracted in tandem toward the handle in order to close the jaws and simultaneously engage the studs against the fasteners to deploy the fasteners. The second trigger may then be retracted relative to the first trigger to disengage the studs from the fastener, and the first and second triggers are moved away from the handle in tandem to open the jaws. An audible confirmation is given when the jaws are fully closed (via a "clicker" as described below) and the jaws are locked to prevent inadvertent opening before the studs have been retracted.

Providing separate triggers as described above is advantageous since it allows jaw closure and opening to be decoupled from stud retraction. In particular, by providing interlocks as described below, the closure device applicator can be configured to provide, in order, (1) jaw closure with fastener deployment, (2) retraction of the studs, and (3) opening of the jaws. It will be appreciated that retracting the studs before the fasteners are deployed or opening the jaws before the fasteners are retracted results in significant risk of procedure failure. The particular ordering of the steps is provided by the specific construction of the linkage assembly as well as inclusion of interlocks and audible feedback when the device is properly deployed.

In the specific examples, the linkage assembly will comprise a pair of sleeves disposed along a fixed rod which together define the shaft joining the triggers to the jaws and studs. Typically, the sleeves are coaxial and the first trigger is connected to move a first sleeve to close the jaws and the second trigger is connected to a second sleeve to disengage the studs. Usually, the first trigger will be pivotally mounted on the handle and the second trigger will be pivotally mounted on the first trigger.

In other specific embodiments, the first trigger is coupled to the first sleeve by a first lever and the second trigger is coupled to the second sleeve by a second lever. Preferably, an interlock is disposed between the first trigger and the handle such that the interlock is engaged when the first and second triggers are retracted in tandem to close the jaws and is released when the second trigger is retracted relative to the first trigger to retract the studs. The interlock prevents the accidental opening of the jaws before the studs have been retracted using the second trigger.

In a second aspect of the present invention, a closure device for closing a compression body over a left atrial appendage comprises a shaft, a pair of jaws pivotally connected to a distal end of the shaft, a handle attached to a proximal end of the shaft, and a triggering mechanism on the handle coupled to the jaws to close the jaws and deploy the compression body over the left atrial appendage. In order to facilitate introduction of a compression body carried on the jaws via an intercostal penetration to the left atrial appendage, the jaws are configured to open and close in a plane disposed at an angle in a range from 10° to 20°, typically 15°, relative to an axis of the shaft. This angle allows the shaft to be introduced at a corresponding angle relative to an anterior-posterior plane of the patient's body, where the anterior-posterior plane is perpendicular to the sagittal plane. This improvement resulted from the discovery by the inventor herein, when using the designs disclosed in prior co-pending application 2007/0260278 that deployment jaws oriented in axially aligned plane would be difficult to position in intercostal delivery protocols. In particular, The angled jaws allow the closure member to be aligned across the base of the left atrial appendage so that the os in the wall of the left atrium can be completely closed to be free from cul-de-sacs.

In still further aspects of the present invention, systems comprise a closure device such as those described in co-pending, commonly-owned US 2007/0260278, and any of the device applicators described above.

Methods according to the present invention for closing a tissue structure comprise positioning a compression body over the tissue structure, such as a left atrial appendage, with at least two compliant tissue-engaging surfaces engaging opposite sides of the tissue structure. The first trigger coupled to a pair of jaws holding the compression body is pulled to close the jaws and deploy a plurality of fasteners between the tissue-engaging surfaces and through the tissue structure. The second trigger is then pulled to disengage the plurality of studs on the jaws from contact with the fasteners, and the first trigger is released to open the jaws and release the compression body. Preferably, at least the first and second triggers may be selectively interlocked to prevent opening of the jaws until the studs have been released.

Further methods according to the present invention for closing the base of a left atrial appendage comprise inserting a shaft through a intercostal incision toward the left atrial appendage. Jaws carrying a compression body are positioned over the left atrial appendage, where the jaws are actuable in a plane disposed at an angle in the range from 10° to 20°, typically 15°, relative to the axis of the shaft. The jaws are then closed to deploy the compression body over the left atrial appendage. The advantages of the angled jaws are discussed above.

DETAILED DESCRIPTION OF THE INVENTION

The present invention provides alternative and improved apparatus, systems, and methods for deploying a closure device over a tissue structure of a patient, for example, a left atrial appendage in a patient at risk of stroke or other adverse events resulting from emboli released into circulation from the left atrial appendage. Patients benefiting from the procedures of the present invention will include those suffering from atrial fibrillation which can cause clot and thrombus formation in the left atrial appendage, thus increasing the chance of emboli release.

The present invention provides a closure device applicator for introducing the closure device over the base of the tissue structure and left in place to close the tissue structure at the base. The portion of the tissue structure which is over the base may then be excised or otherwise removed, although this may be left be left to the physician's preference. The tissue closure device comprises a compression body having at least two opposed, compliant tissue-engaging surfaces which will be placed over opposite sides of the tissue structure. The tissue-engaging surfaces will be held together by a plurality of axially spaced-apart tissue-penetrating fasteners which extend from one of the surfaces, through the intermediate tissue, and into the other surface to both hold the compression body in place and to apply a desired level of compression force, which is determined by both the softness of the compression body and the distance between the surfaces when they are fully attached. A well may be provided in the compression body around the tissue-penetrating barb of the fastener such that a gasket seal is formed by the compression body around the puncture site in the tissue. A stabilizing lip may be provided in one leg of the compression body to prevent a rolling motion of one leg with respect to another leg of the compression body which keeps the two opposing soft members linearly aligned. More detailed descriptions of the closure devices are found in commonly owned, co-pending US 2007/0260278, the full disclosure of which has been previously incorporated herein by reference.

Figure 1:
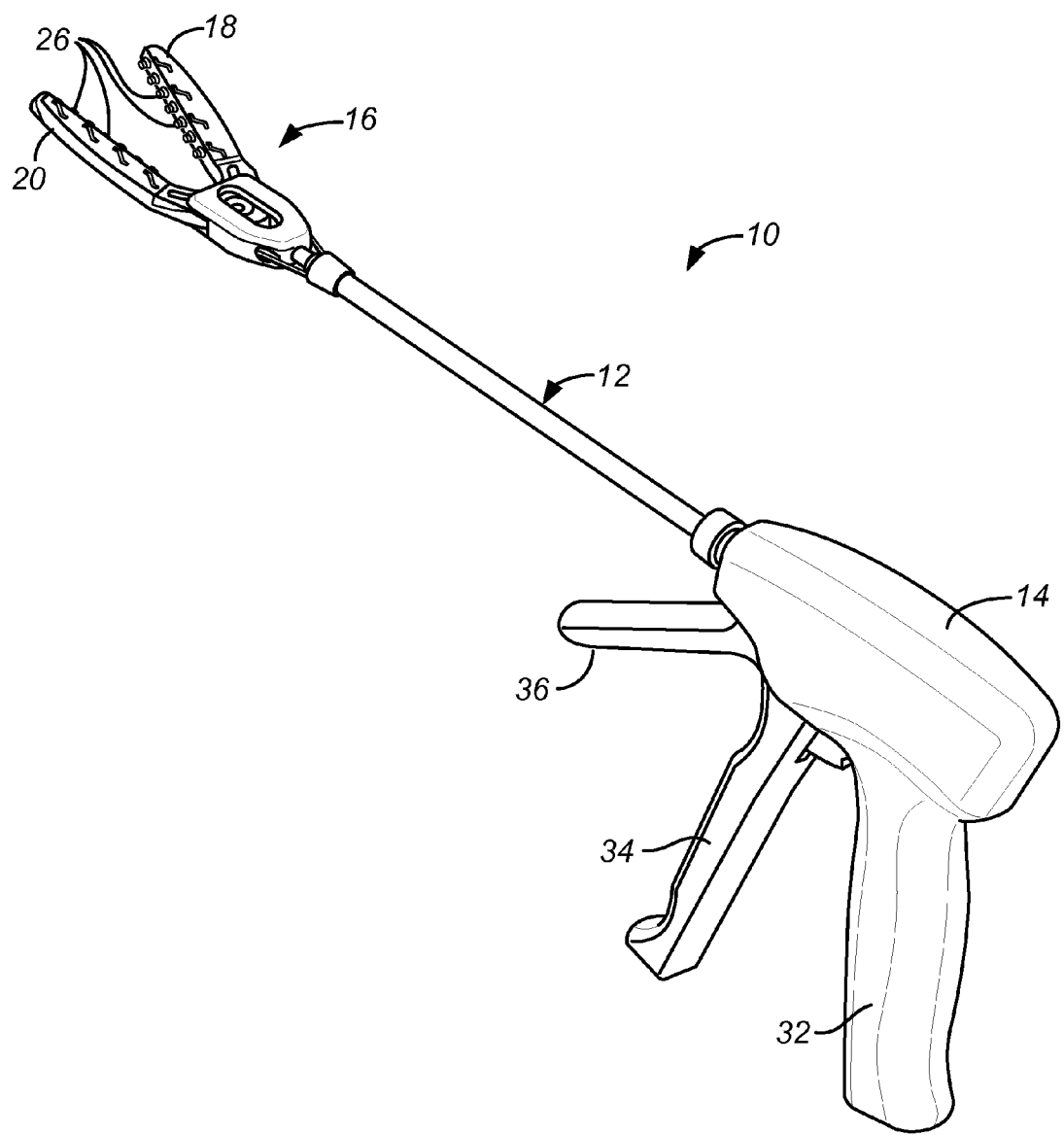
FIG. 1 is a perspective view of a closure device applicator constructed in accordance with the principles of the present invention.
Figure 2:
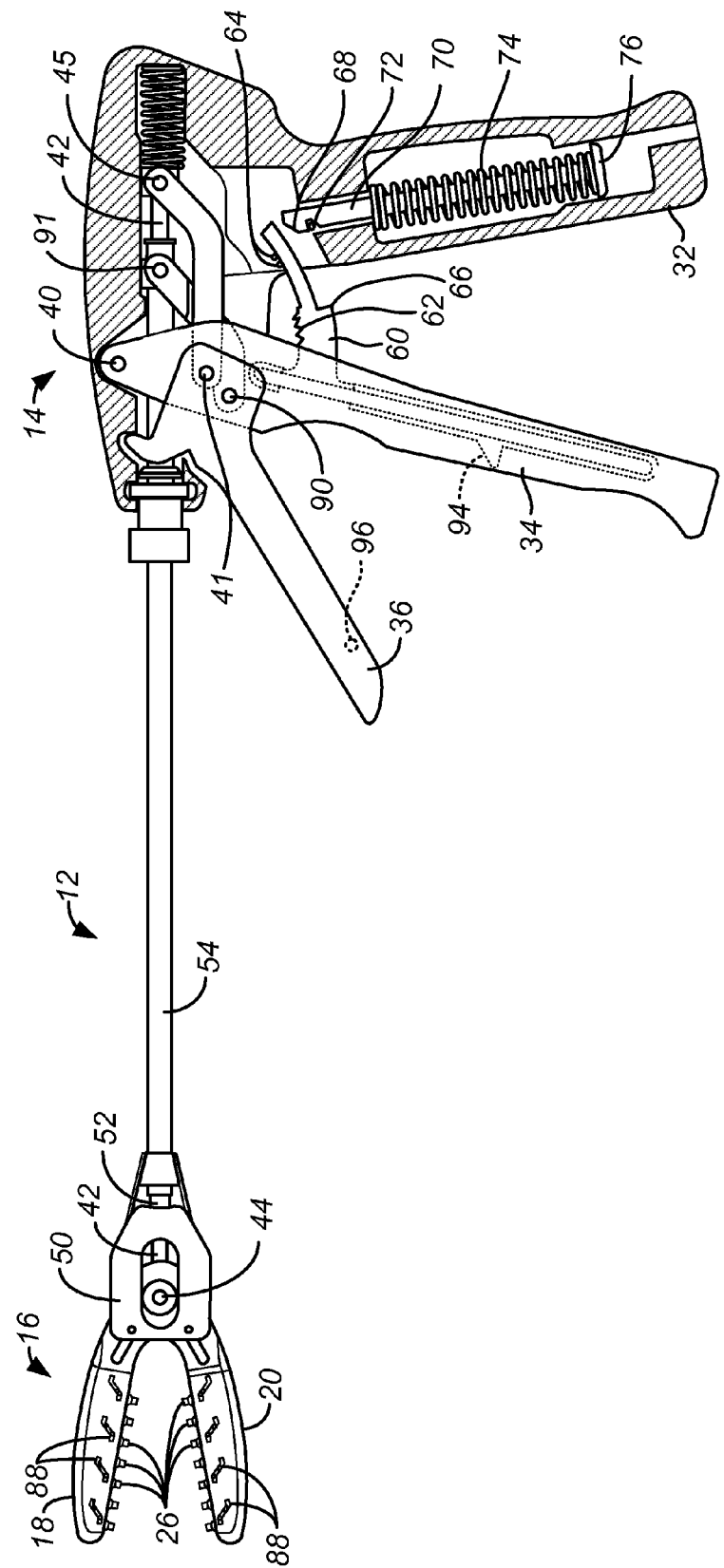
FIG. 2 is a partial cross-sectional view of the closure device applicator of FIG. 1, shown with the jaws open and rotated 90° relative to the position shown in FIG. 1.
Figure 6A:
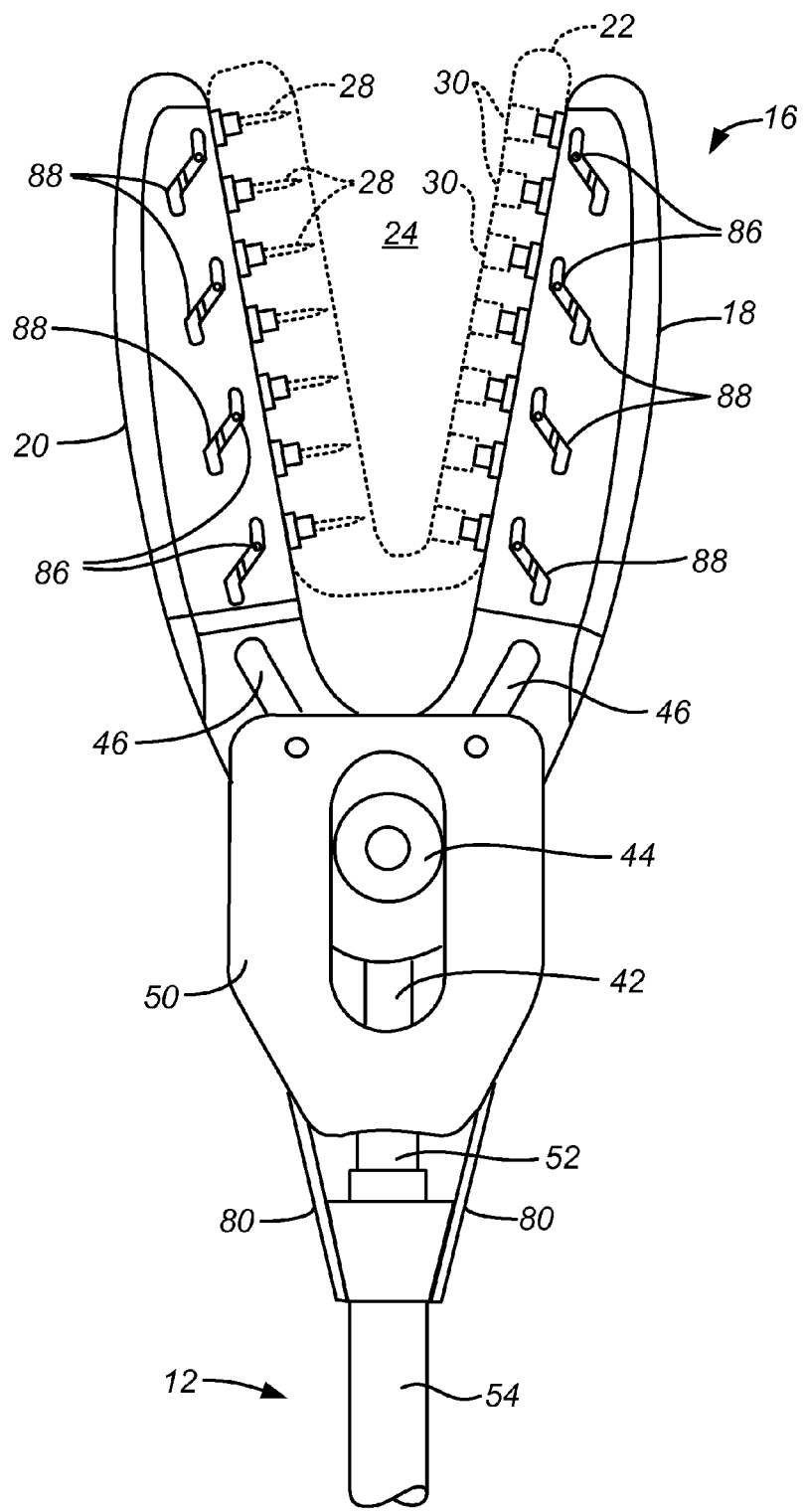
FIGS. 6A-6D illustrate the movement of the jaw and stud engagement with the fasteners of a tissue closure device.

Referring now to FIG. 1, a closure device applicator 10 constructed in accordance with the principles of the present invention comprises shaft assembly 12 having a handle assembly 14 at its proximal end, and a jaw assembly 16 at a distal end, where individual jaws 18 and 20 are adapted to carry a closure device 22, as best illustrated in FIG. 6A-6D. The closure device 22 has a U-shaped configuration which defines a V-shaped region 24 for receiving the left atrial appendage or other tissue structure when the jaws are open as shown in FIGS. 1, 2, and 6A. A plurality of studs 26 are formed along the inner surfaces of each jaw 20 and 18 to engage tissue-penetrating fasteners which comprise penetrating components 28 and receptacle components 30, as best shown in FIG. 6A. The handle assembly 14 will include a handle 32, a first trigger 34, and a second trigger 36.

Referring now to FIGS. 2 and 6A, the closure device applicator 10 is shown in its shelf or delivery configuration with the closure device 22 received over the jaw assembly 16 and the V-shaped opening 24 in the device ready to be placed over a left atrial appendage (see FIG. 8) or other tissue structure. The first trigger 34 and second trigger 36 are fully open, that is, pivoted fully away from the handle 32.

Figure 3:
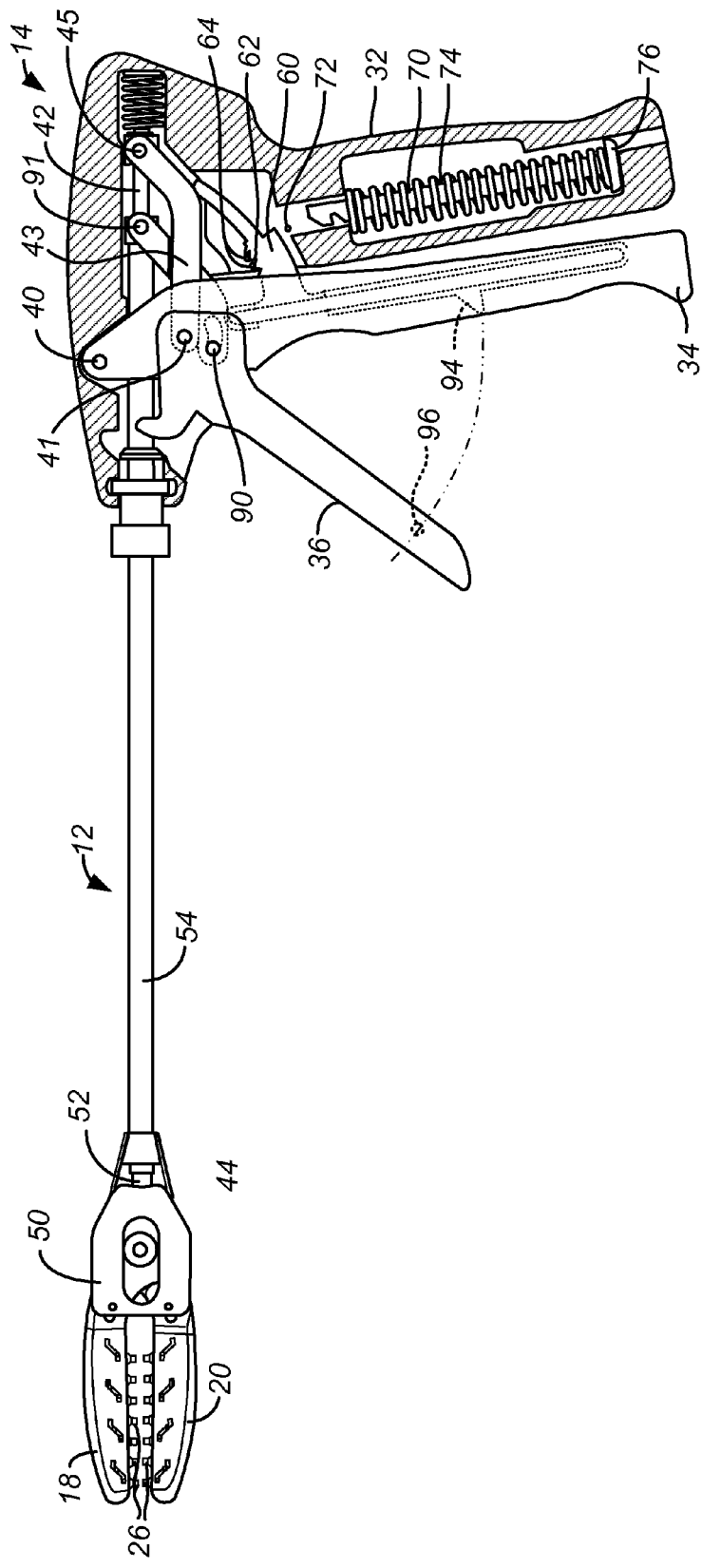
FIG. 3 is a partial, cross-sectional view of the device applicator similar to FIG. 2, shown with the first and second levers closed relative to the handle in order to close the jaws.
Figure 6B:
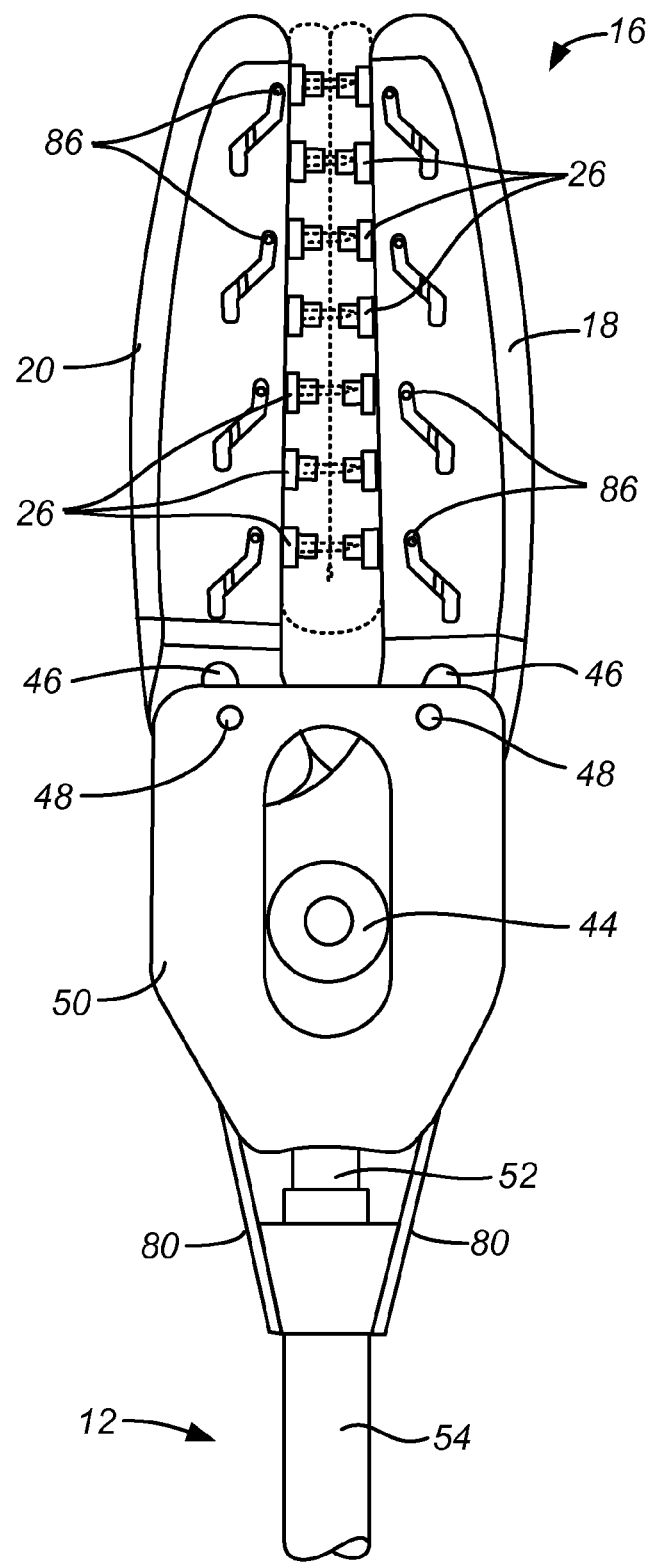

After the closure device 22 has been advanced over the left atrial appendage or other target tissue structure, the jaws 18 and 20 will be closed by manually pulling first trigger 34 toward handle 32, as shown in FIGS. 3 and 6B. Trigger 34 is mounted on a pivot 40 which is fixedly secured to the handle assembly 14. Closing the trigger 34, that is, pivoting on pivot 40, proximally retracts rod 42 which is linked to the trigger by pin 41 and lever 43. Rod 42 is attached to a pin 44 (FIG. 6B) which is pivotally attached to the proximal ends of jaws 18 and 20 and proximally retracts the jaws so that they are closed by the movement of slots 46 over pins 48 in an end frame 50 attached to a stationary sleeve 52. When the jaws 18 and 20 are closed, the studs 26 engage the tissue penetrating components 28 and tissue penetrating receptacles 30 so that they engage and lock with each other, thus closing the two legs of the closure device 22, as shown in FIG. 6B. The second trigger 36 is mounted on the pin 41 so that it closes in tandem with the first trigger 34.

As the first trigger 34 and second trigger 36 are closed in tandem, an interlock 60 having a ratcheting tooth surface 62 is closed against pins 64, as shown in FIG. 3, so that the trigger 34 cannot be opened once the jaws have been closed. This is advantageous as described above, since the jaws should not be opened prior to retracting the studs 26 by closing the second trigger 36, as will be described below.

Additionally, as the first trigger 34 is closed to close the jaws 18 and 20 of the jaw assembly 16, a corner 66 (FIG. 7) of the interlock 60 will engage an inclined surface 68 on a clicker pin 70 to disengage the clicker pin from a holding pin 72, thus allowing spring 74 to push the pin 70 downward so that a bottom surface 76 strikes the bottom of the handle, thus causing a loud click to audibly alert the physician that the jaws have been closed and the interlock has been engaged. This audible confirmation indicates to the physician that the closure device 22 has been closed and that the studs 26 can be retracted.

Figure 4:
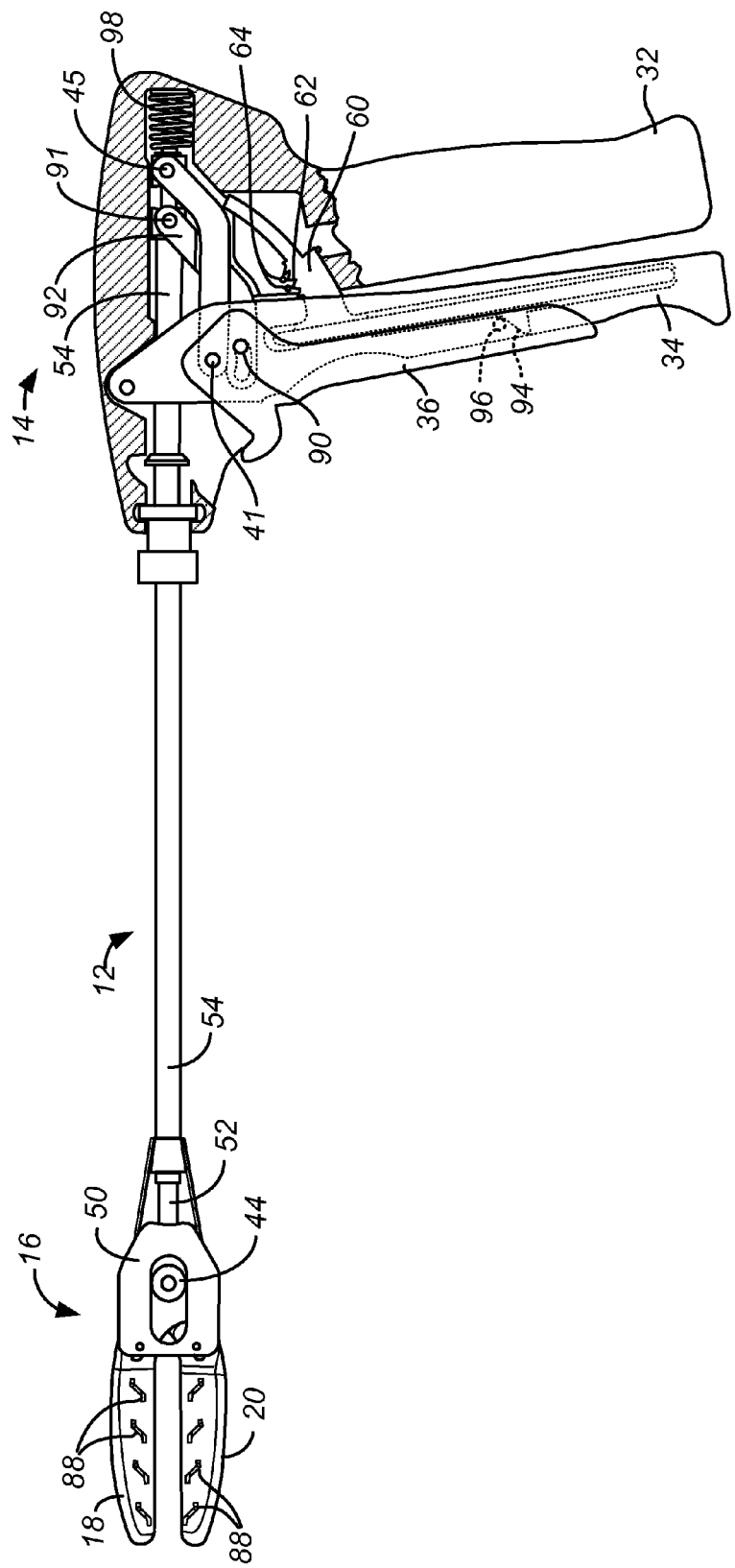
FIG. 4 is a partial, cross-sectional view of the closure device applicator similar to that shown in FIGS. 2 and 3, with the second trigger closed relative to the first trigger in order to retract the fastener-engaging studs.
Figure 6C:
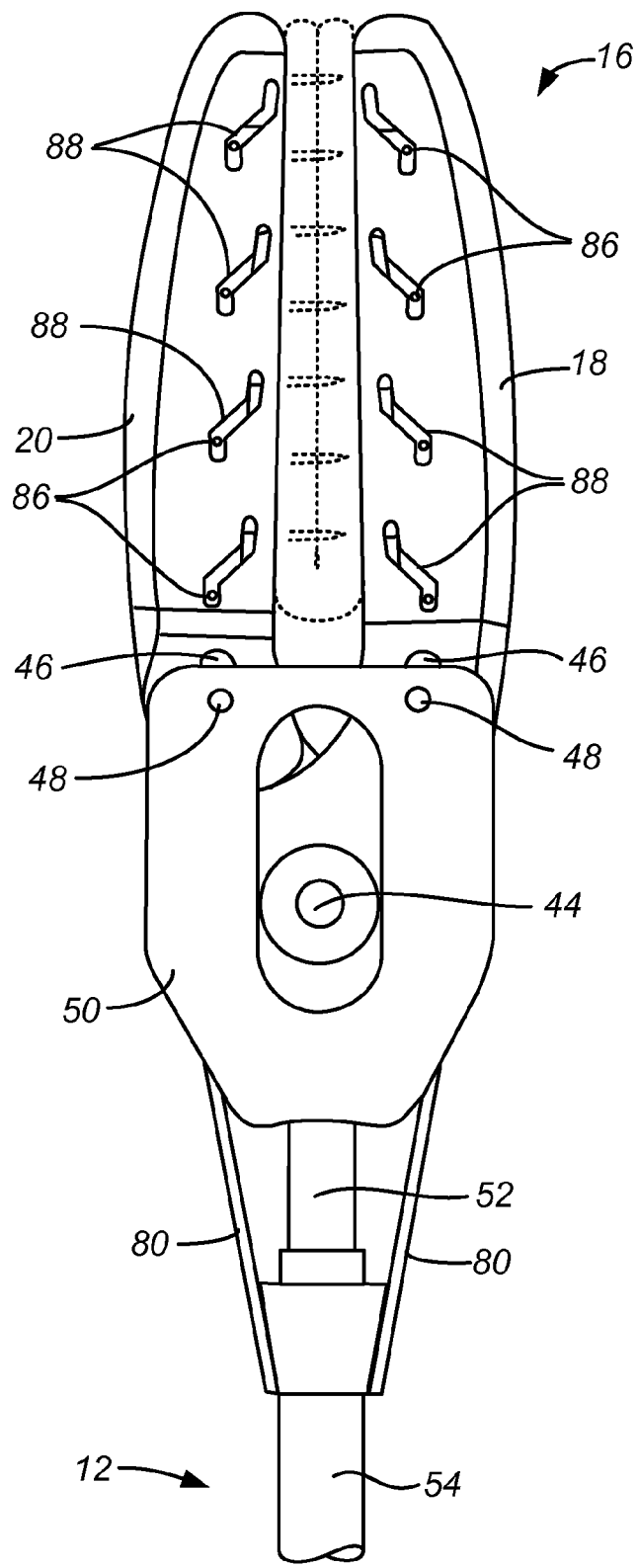
Figure 6D:
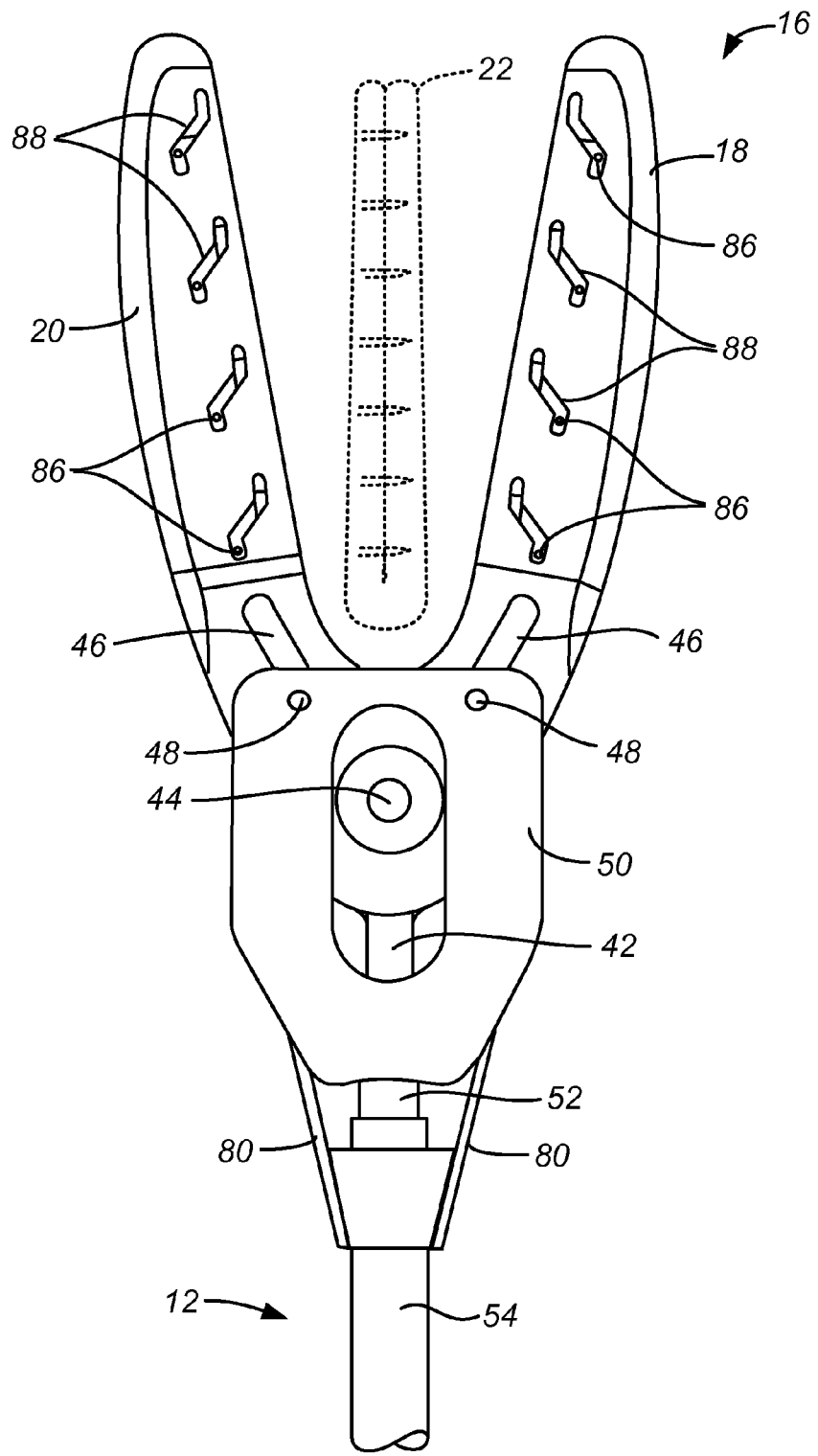
Figure 7:
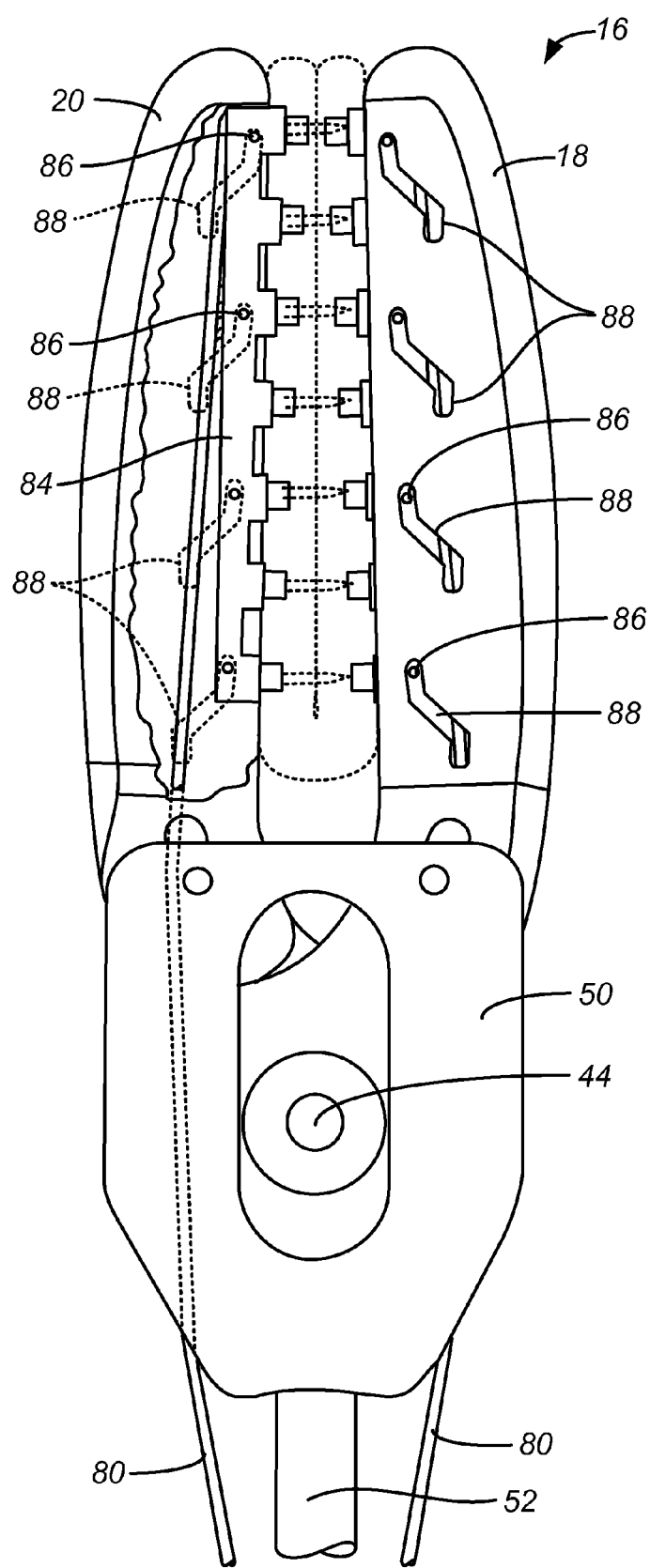
FIG. 7 illustrates the mechanism by which the fastener-engaging studs are retracted within the jaws.

Referring now to FIGS. 4 and 6C, the studs 26 are retracted by closing second trigger 36 against the first trigger 34, as shown in FIG. 4. Closure of the second trigger 34 draws outer sleeve 54 proximally over stationary sleeve 52 which draws pull wires 80 proximally to pull stud comb 84 proximally, as shown in FIG. 7. The stud combs 84 are mounted on pins 86 which travel in slots 88 formed in each of the jaws 18 and 20. The second trigger 36 is pivotally mounted on the first trigger by a pin 41 and is coupled to the stationary sleeve by pins 90 and 91 and lever 92.

Figure 5:
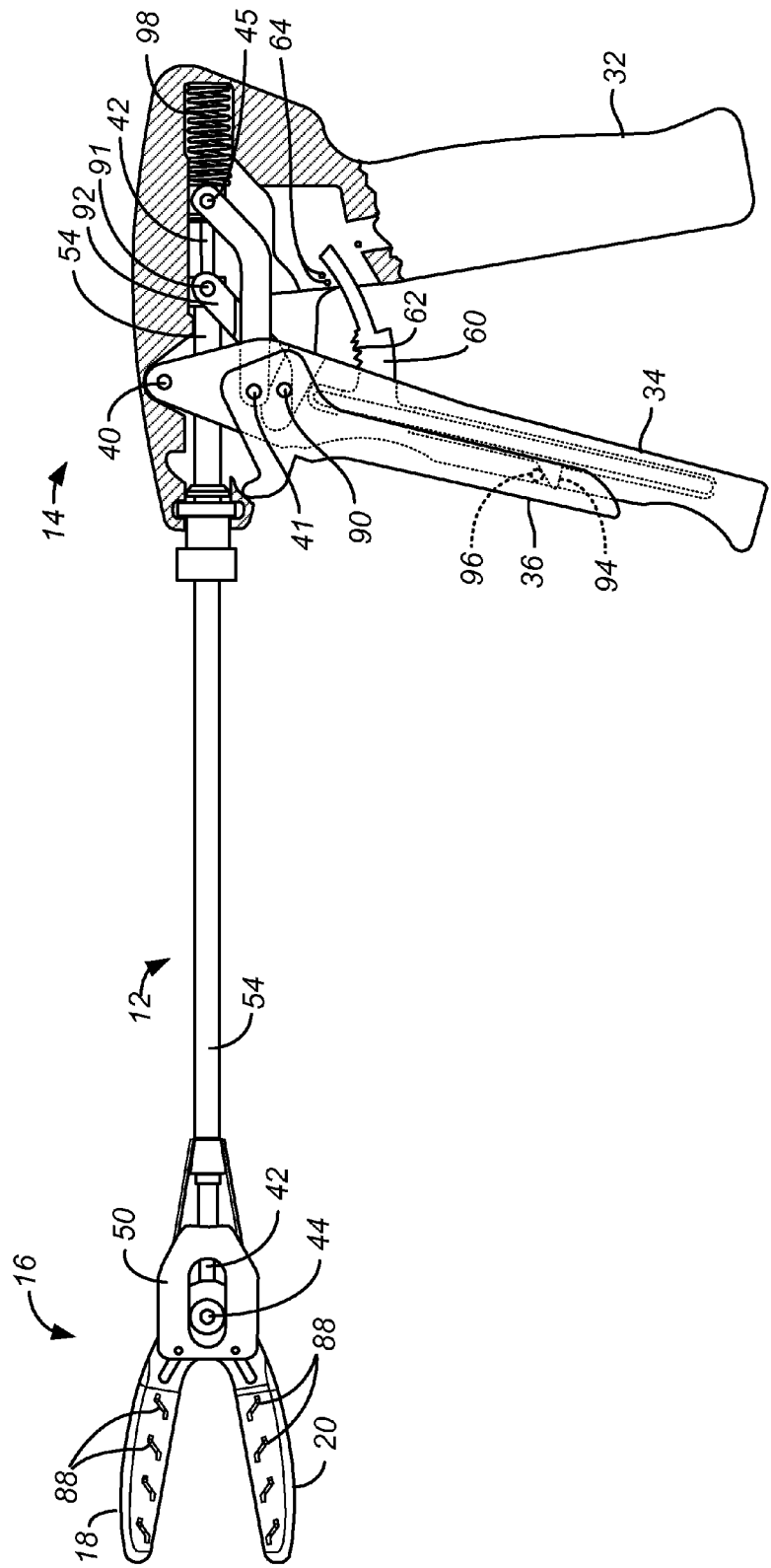
FIG. 5 is a partial, cross-sectional view of the closure device applicator of FIGS. 2-4, shown with the first and second triggers re-opened in order to open the jaws while the fastener-engaging studs remain retracted.

Closure of the second trigger 36 disengages the interlock 60 by engaging a ramped surface 94 attached to the interlock against a fixed pin 96 in the second trigger. The pin 96 follows the path shown in broken line in FIG. 3 to engage the surface 94. The ramped surface 94 is caused to move downwardly, pulling the ratchet teeth 62 away from the fixed pins 64, as shown in FIGS. 4 and 5. The triggers 34 and 36 are now ready to be opened in order to open the jaws, as will now be described.

Referring now to FIGS. 5 and 7C, the jaws 18 and 20 may be opened by releasing manual compression on the first and second triggers 34 and 36, allowing spring 98 which was compressed during closure of the first trigger 34 to push rod 42 (attached to pivot 44) distally forward, opening the jaws and leaving the closure device 22 in place.

Figure 8:
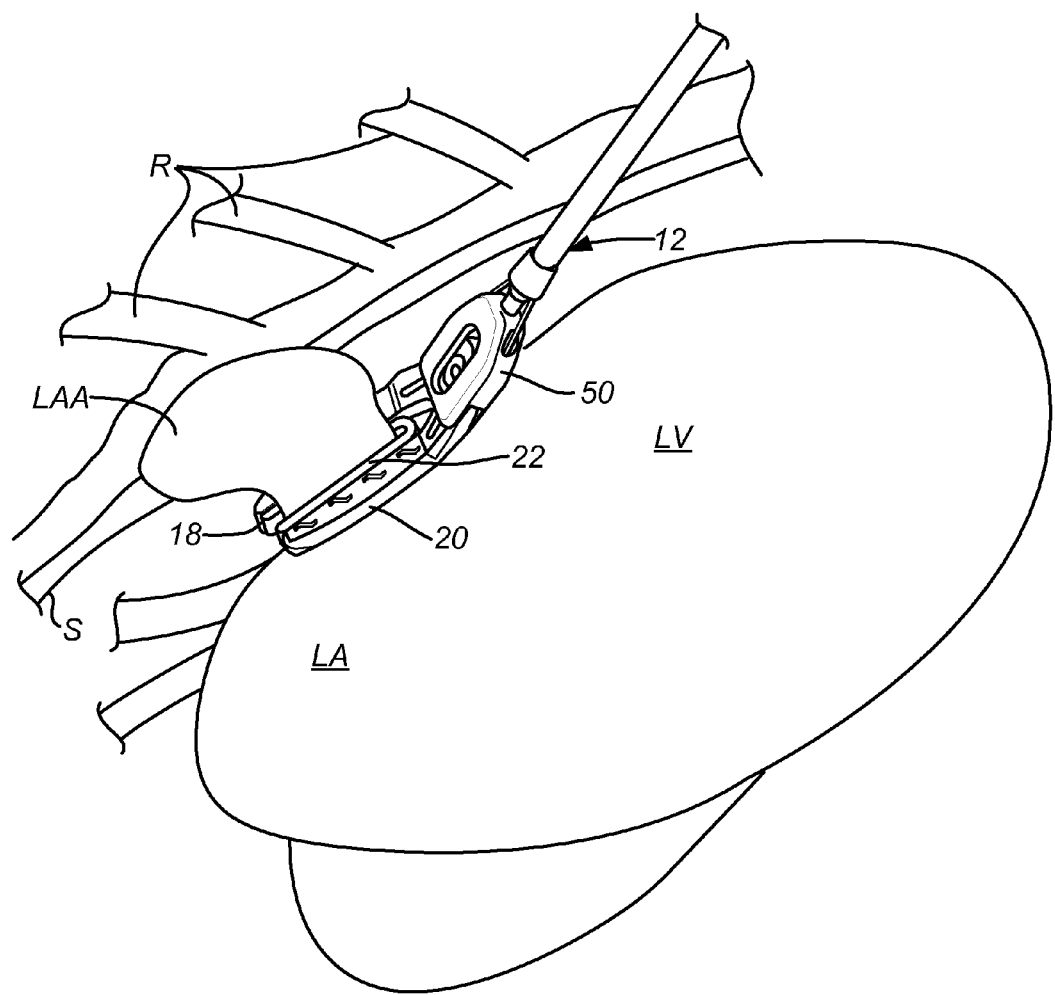
FIG. 8 illustrates use of the closure device applicator of the present invention for closing a closure device over a left atrial appendage in accordance with the principles of the present invention.

Referring now to FIG. 8, the closure device applicator of the present invention can be used to deliver a closure device 22 over the base of a left atrial appendage LAA in an open chest, beating heart procedure. The sternum S is opened, spreading the ribs R to provide a working space over the heart. After opening the pericardial sack, the heart may be lifted and turned, for example using a sheet of gauze or other material which is placed behind the heart, to expose the left atrial appendage within the opening as shown in FIG. 8. After the left atrial appendage LAA is exposed, the jaws 18 and 20 of the closure device applicator are placed around the base of the appendage by manipulating the shaft 12, as shown in FIG. 8.

The angle of the jaws 18 and 20 relative to the shaft, typically about 15°, is highly advantageous as it allows the jaws to engage the base of the left atrial appendage so that they are generally parallel with the os between the appendage and the left atrium LA. If the plane of the jaws was aligned with the shaft, it would be difficult to achieve this orientation and the risk of closing the appendage and leaving a cul-de-sac (an open space beyond the os and into interior of the left atrial appendage) is greatly increased. Such cul-de-sac is problematic as it can be a source of clotting and, if created, must be closed in the same or later procedure. Once the jaws 18 and 20 properly position the closure device 22 about the base of the left atrial appendage, the jaws are actuated and the closure device deployed as described previously.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A closure device applicator for use with a closure device including a compression body having two legs with opposed tissue-engaging surfaces and a plurality of tissue-penetrating fasteners deployable between said surfaces, said applicator comprising:
   a shaft;
   a handle attached to a proximal end of the shaft with a first trigger and a second trigger;
   a pair of jaws pivotally attached to a distal end of the shaft, each jaw having a plurality of retractable studs, wherein the jaws are adapted to removably hold the closure device with the studs engaging the fasteners in the closure device; and
   a linkage assembly joining the handle to the pair of jaws, wherein the first trigger and the second trigger are retracted in tandem toward the handle to close the jaws and deploy the fasteners, the second trigger is retracted relative to the first trigger to disengage the studs from the fasteners, and the first and second triggers are moved away from the handle in tandem to open the jaws.

2. An applicator as in claim 1, wherein the linkage assembly comprises a pair of sleeves disposed along the shaft, and joining the triggers to the jaws and studs.

3. An applicator as in claim 2, wherein the sleeves are coaxial.

4. An applicator as in claim 3, wherein the first trigger is connected to move a first sleeve to close the jaws and the second trigger is connected to a second sleeve to disengage the studs.

5. An applicator as in claim 4, wherein the first trigger is pivotally mounted on the handle.

6. An applicator as in claim 5, wherein the second trigger is pivotally mounted on the first trigger.

7. An applicator as in claim 6, further comprising a first lever coupled between the first trigger and the first sleeve and a second lever coupled between the second trigger and the second sleeve.

8. An applicator as in claim 1, further comprising an interlock between the first trigger and the handle, wherein the interlock is engaged when the first and second triggers are retracted in tandem and is released when the second trigger is retracted relative to the first trigger.

9. An applicator as in claim 1, wherein the jaws open and close in a plane disposed at an angle in the range from 10° to 20° relative to an axis of the shaft.

10. An applicator as in claim 9, wherein the linkage assembly comprises a wire connected between the second trigger and the studs, wherein the wire conforms to the angle between the jaws and the shaft.

11. A system comprising:
    a closure device; and
    an applicator as in any one of claims 1 to 10.

12. A left trial appendage isolation system for isolating a left atrial appendage, said left atrial appendage isolation system comprising:
    a shaft;
    a first jaw and a second jaw located at a distal end of the shaft, wherein one of the first and second jaws is adapted to move with respect to the other;
    a plurality of studs moveable with respect to at least one of the jaws; and
    a triggering mechanism operatively associated with one of the first and second jaws to close the jaws relative to one another and when a compression body comprising fasteners configured to pierce tissue is positioned between the first and second jaws, to deploy the compressing body over the left atrial appendage; and
    wherein the triggering mechanism is configured to cause the following actions in order upon actuation and when the compression body is positioned between the first and second jaws: (i) closure of the jaws relative to one another and deployment of the fasteners, (ii) retraction of the studs from the fasteners, and (iii) opening of the jaws relative to one another.

13. The system of claim 12, wherein the first an second jaws open and close relative to one another in a first plane, the first plane disposed at an angle offset with respect to a second plane that passes through an axis of the shaft.

14. The system of claim 12, wherein the compression body has two legs.

15. The system of claim 12, wherein the triggering mechanism comprises:
    a first trigger assembly operatively associated with at least one of the first and second jaws to close the jaws relative to one another and deploy the compression body; and
    a second trigger assembly configured to release the compression body from the first and second jaws, wherein the second trigger assembly is operatively associated with the first trigger assembly.

16. The system of claim 15, further comprising:
    the compression body; and
    wherein the first trigger assembly comprises a trigger for closing the first and second jaws relative to one another and deploying the compression body upon moving the first trigger from a first position to second position.

17. A left atrial appendage closure system adapted for isolating a left atrial appendage with a closure device, the closure device comprising a first portion with a penetrating component to penetrate tissue and a second portion with a receptacle component for receiving the penetrating component, the left atrial appendage closure system comprising:
    a first jaw acrd a second jaw extending from a distal region of the applicator, at least one of the first and second jaws is moveable with respect to the other of the first and second jaws, the first jaw comprises a plurality of studs capable of at least partially retracting with respect to the first jaw wherein the first and second jaws are adapted to removably engage the closure device;
    a first trigger and a second trigger each having a first position and a second position; wherein movement of the first trigger from the first position to the second position moves the jaws into closer proximity to each other and movement of the second trigger from the first position to the second position causes at least partial retraction of the studs; and a interlock configured to maintain the first trigger in the second position after the closure device has been deployed.

18. The system of claim 17, further comprising: an elongate shaft, the first and second jaw connected to a distal region of the shaft and a handle connected to a proximal region of the shaft.

19. A left atrial appendage closure device applicator for use in isolating a left atrial appendage, the applicator comprising:

a pair of jaws extending from a distal region of the applicator, at least one of the jaws configured for pivotal movement with respect to the other of the jaws, the jaws comprising a plurality of studs configured to at least partially retract into the jaws wherein the jaws are adapted to removably engage a closure device configured to pierce through tissue of the left atrial appendage;

a handle attached to a proximal region of the applicator and located proximally with respect to the jaws;

a first trigger moveable with respect to the handle from a first position to a second position to bring one of the jaws in closer proximity to the other of the jaws and to deploy the closure device over the left atrial appendage when moved; and a second trigger movable with respect to the first trigger from a third position to a fourth position; and an interlock mechanism configured to (i) maintain the first trigger in the second position, and (ii) release the first trigger from the second position when the second trigger is moved towards the fourth position.

* * * * *